United States Patent [19]

Ford et al.

[11] Patent Number: 4,970,273

[45] Date of Patent: Nov. 13, 1990

[54] SULPHURYL CHLORIDE/POLYAMIDE DERIVATIVE SUPPORT

[75] Inventors: Douglas L. Ford, Eastwood; Richard Grant, Dundas, both of Australia

[73] Assignee: Memtec Limited, Parramatta, Australia

[21] Appl. No.: 299,985

[22] Filed: Jan. 23, 1989

Related U.S. Application Data

[62] Division of Ser. No. 887,036, Jun. 27, 1986, Pat. No. 4,822,863.

[30] Foreign Application Priority Data

Oct. 29, 1984 [AU] Australia ............................... PG7884

[51] Int. Cl.$^5$ .............................................. C08G 69/48
[52] U.S. Cl. ................................... 525/430; 525/54.1; 525/420
[58] Field of Search ............................... 525/430, 420

[56] References Cited

U.S. PATENT DOCUMENTS 4,822,863 4/1989 Ford ..................................... 525/420

Primary Examiner—Harold D. Anderson
Attorney, Agent, or Firm—Oblon, Spivak, McClelland, Maier & Neustadt

[57] ABSTRACT

A process for producing a support capable of reaction with antibodies or enzymes, said process comprising the steps of:

(i) reacting an aliphatic polyamide with a solution consisting essentially of sulphuryl chloride and a paraffin or cycloparaffin to produce a sulphuryl chloride modified polyamide reactive intermediate product;

(ii) reacting the product of step (i) with a compound that binds to said product to provide a covalent chemical link to which antibodies or enzymes may be bound.

4 Claims, No Drawings

SULPHURYL CHLORIDE/POLYAMIDE DERIVATIVE SUPPORT

This is a division of application Ser. No. 887,036, filed June 27, 1986, now U.S. Pat. No. 4,822,863.

FIELD OF THE INVENTION

This invention relates to the preparation of sulphuryl chloride treated aliphatic polyamides which may be coverted to provide supports for use in affinity chromatography and for immobilizing enzymes.

BACKGROUND ART

Affinity chromatography is a separation technique based on the reversible, specific interaction of a biological substance in solution or suspension when passed through a subdivided filling holding a complementary biological substance.

Most prior work on affinity chromatography has used a filling comprised of small beads of agarose. Extensive literature exists on means of activating the agarose with suitable chemicals to provide a covalent chemical link for the binding of an antibody so that harvesting of the desired antigenic protein is possible. After the desired antigenic protein has been bound to the filling containing the covalently bonded antibody impurities are washed away and the desired pure antigenic protein is eluted by a solution from which it is easily separated. The eluting solution should leave the filling containing the covalently bonded antibody ready for reuse.

Immobilized enzymes are enzymes suitably held on an extensive surface of the filling and have reached industrial scale use. The support matrix used is often a membrane of suitable shape and porosity. Steric requirements usually dictate that a suitable spacer arm be provided between the support matrix and the covalent chemical link to the enzyme to give high efficiency and selectivity. Suitable spacer arms and the activating chemicals required are described by O. R. Zaborsky in "Immobilised Enzymes", C.R.C. Press, Cleveland, Ohio, 1974.

Canadian Pat. No. 1,083,057 deals with the prior art of forming some suitable porous membranes, their activation and a method of reacting the enzyme whilst forcing it through the membrane.

Although nylons are physically very suitable as a support matrix because of tolerance of sterilising temperatures, stiffness, hydrophilicity and ease of forming, they have been little used since they are difficult to activate, particularly if isothiocyanate end groups are needed.

The reaction of sulphuryl chloride on the polyamide fibre Nylon 6 has been investigated by D. S. Varma and Thomas Eapen. As reported in the Indian Journal of Textile Research, Vol. 1, March 1976, pp. 26–28 their findings were:

"Our results thus indicate that the reaction of Nylon 6 with sulphuryl chloride is accompanied by predominant chain scission reactions. Cross-bond formation is indicated by the appearance of an additional peak in the DTA thermogram. As a result of hydrolysis, a deterioration in the properties is observed."

These unpromising results confirm the earlier work of S. A. M. El-Garf and Y. Abou-Street in Faserforschung Textiltechnik Vol. 25(6), pp. 248–51, 1974 where it was reported that degradation increased as the temperature increased. Furthermore, the rates of reaction and of degradation were higher in carbon tetrachloride than in toluene.

The Varma and Eapen paper contains no suggestion of useful, reactive intermediates being prepared by the reaction of sulphuryl chloride on Nylon 6.

American Chemical Abstracts record no reactions of sulphuryl chloride with monomeric aliphatic secondary amides, thus giving no expectation of useful intermediates being formed by the reaction of sulphuryl chloride on aliphatic polyamides.

DISCLOSURE OF THE INVENTION

We have surprisingly found that sulphuryl chloride may be used as a convenient, economical reactant to convert the surface of aliphatic polyamides into suitable intermediates which may then be converted into stable ready-to-use supports capable of direct reaction with antibodies or enzymes.

According to one aspect of the invention aliphatic polyamides are reacted on their surfaces in anhydrous conditions with sulphuryl chloride, either neat or in solution in paraffins or cycloparaffins, to give reactive intermediates which were suitable for preparing derivatives for affinity chromatography. These derivatives were found to be stable and could be designed to contain ready-to-use spacer arms and a variety of terminal functional groups able to combine covalently with antibodies or enzymes The invention thus provides a process for preparing supports capable of reaction with antibodies or enzymes comprising the steps of:
  (i) reacting an aliphatic polyamide with sulphuryl chloride to form an intermediate, and,
  (ii) converting the intermediate into the support by providing thereon a covalent chemical link to which the antibodies or enzymes may be bound The invention also provides a support capable of reaction with antibodies or enzymes comprising an aliphatic polyamide reacted with sulphuryl chloride and having thereon a plurality of covalent chemical links to which the antibodies or enzymes may be bound.

The supports may be supplied in sterile form, in suitable shape and porosity and require no special activation procedure to provide spacer arms ending in chemical groups capable of reacting covalently with the terminal groups of enzyme or antibody proteins.

The spacer arms may be provided by reacting the intermediate with 1,6-diaminohexane and the covalent chemical link by further reacting with glutaraldehyde. In one form of the invention, the spacer arm and covalent chemical link are formed by reacting the intermediate with 4-hydroxybenzaldehyde.

DESCRIPTION OF PREFERRED EMBODIMENTS

The preferred methods of the invention to provide the reactive intermediates and to convert the intermediates to a useful range of protein-binding fillings will now be illustrated by the following examples. All the examples were performed on a woven Nylon 6 membrane of pore size around 5 microns. In all cases after staining to confirm functionality, the membrane was washed with water, boiled in ethanol and then washed again in water. Only then was a final assessment made of the stainability of the membrane.

EXAMPLE 1

The membrane was soaked in a solution of 25% sulphuryl chloride in petroleum spirit (b.p. 40°–60° C.) at 45° C. for 5 minutes. It was then washed in petroleum spirit and dried at 65° C. for 10 minutes. The product was tacky to touch and stuck readily to itself. A small portion of the material stained blue in an aqueous solution of Methylene Blue stain, indicating the presence of sulphonyl chloride groups. This membrane changed its properties after several hours in air, presumably due to hydrolysis of the pendant sulphonyl chloride groups. It was thus convenient to store it under petroleum spirit until used as an intermediate.

EXAMPLE 2

The membrane obtained as described in Example 1 was soaked in a molten mass of 1,6-diaminohexane at 65° C. for 1 hour. It was then washed thoroughly in water. The presence of pendant amino groups (as spacer arms) was demonstrated by staining with an aqueous solution of 4-nitrobenzenediazonium tetrafluoroborate.

EXAMPLE 3

The membrane obtained as described in Example 1 was soaked in an aqueous solution of potassium hydroxide (0.5%) and 4-hydroxybenzaldehyde (1.12%) for 15 minutes at room temperature. The membrane was then washed thoroughly in water. The presence of aldehyde groups in the membrane was confirmed by staining with 2,4-dinitrophenylhydrazine reagent. The stained membrane darkened on immersion in aqueous sodium hydroxide solution (10%), confirming the initial presence of aldehyde groups.

EXAMPLE 4

The membrane obtained as described in Example 2 was soaked for 8 hours in hexamethylene diisocyanate at room temperature. The membrane was then washed thoroughly in ether. A small sample of this membrane failed to stain with 4-nitrobenzenediazonium tetrafluoroborate solution. This confirmed the expected conversion of all original amino groups into a urea spacer arm, terminated by an isocyanate group.

EXAMPLE 5

The membrane obtained as described in Example 2 was soaked for 15 hours at room temperature in 2,3-epoxy-1-chloropropane (epichlorhydrin). It was then washed thoroughly in ether. The sequence of staining treatment changes described in Example 4 confirmed the presence of epoxide groups on the membrane

EXAMPLE 6

The membrane of Example 2 was reacted with 25% glutaraldehyde for 15 hours at 20° C. at pH b 7 and then well washed with water. The presence of aldehyde groups in the membrane was confirmed by staining with 2,4-dinitrophenylhydrazine reagent. The stained membrane darkened on immersion in aqueous sodium hydroxide solution (10%), confirming the initial presence of aldehyde groups.

EXAMPLE 7

The membrane of Example 2 was dried in an oven at 60° and reacted at 20° with a solution of 5% sebacoyl-chloride in dry ether. The product was immersed in water at 20° C. for 10 hours to hydrolyse the resulting acid chloride to the carboxylic acid. The presence of the acid groups was confirmed by titrating a washed portion with dilute alkali to a phenolphthalein end-point as well as by staining with methylene blue solution.

The acidic membrane was freed of water by washing three times for thirty minutes in dry dioxane, followed by draining. Five grams of the dry acidic membrane were treated in 25 ml of dry dioxane with 0.6 g. of N-hydroxysuccinimide and shaken until this dissolved. Then 1 g. of dicyclohexycarbodimide were added and shaken for ½ hour. The resulting membrane was washed four times with dry dioxane, then four times with dry methanol, then twice again with dioxane. Before use as a N-hydroxy-succinimide ester activated support the membrane was drained of free dioxane. Dry tetrahydrofuran can be used in place of the more toxic dioxane.

EVALUATION OF EXAMPLES

The membranes of Examples 3, 4, 5, 6 and 7 were then evaluated as protein immobilization supports These attachment studies were performed using a monoclonal antibody (IgG class) directed against a medium molecular weight protein antigen. 5/16" discs were prepared from each membrane.

Triplicate samples were incubated together in 0.5 ml solution containing 50, 200, or 300 micrograms per millilitre monoclonal antibody (MAb) and a known amount of $125_{I-MAb}$. After agitating for 24 hours the discs were washed to remove non-covalently bound MAb, then treated with ethanolamine to fill vacant active sites. Measurement of the radioactivity of each disc allowed the uptake of MAb to be quantified.

Samples of unactivated nylon were similarly treated to account for non-specific adsorption to the polymer.

Two of the three discs from each of the previous experiments were incubated in 0.5 ml solution containing antigen and $^{125}$I-labeled antigen. The third disc was placed in 0.5 ml buffer to observe MAb desorption. After overnight incubation, the level of radioactivity bound to each disc was determined and the difference between counts prior to antigen attachment was used as a measure of antigen adsorption.

As a test of the strength of the covalent bond between polymer and MAb, the discs were incubated in 4 Molar NaSCN, a commonly-used chaotropic elutant. Satisfactory levels of MAb remaining after this treatment should indicate a bond of acceptable strength.

The results of these tests are shown in Table I. The supports made in accordance with Examples 3, 4, 5, 6 and 7 compared favourably with the agarose gel beads commonly used, especially on activity. The main advantages are the resistance to compression which limits the depth of present gels, the high flow rates allowable and the ability to adapt the shape and the porosity to meet the engineering needs of large scale use.

TABLE I

| EXAMPLE | Initial Antibody Concentration Microgram/ml | Covalently Bound Antibody | | Activity Percent ($n = 2$) | % Antibody Remaining After 4 Molar NaSCN ($n = 1$) |
|---|---|---|---|---|---|
| | | Microgram/cm$^2$ *($n = 3$) | Microgram/gram ($n = 3$) | | |
| 3 | 200 | 1.6 ± 0.2 | 290 ± 25 | 12 ± 1 | 83 |
| 4 | 200 | 6.5 ± 0.5 | 1150 ± 90 | 8 ± 1 | 88 |
| 5 | 200 | 4.2 ± 0.4 | 740 ± 65 | 6 ± 1 | 92 |
| 6 | 50 | 4.0 ± 0.5 | 710 ± 85 | 16 ± 0.5 | 95 |
| 6 | 200 | 10.0 ± 1.3 | 1770 ± 233 | 4 ± 1 | 96 |
| 6 | 300 | 13.7 ± 3.4 | 2400 ± 600 | 4 ± 1 | 96 |
| 7 | 200 | 0.5 ± 0.2 | 91 ± 25 | not done | 98 |

*NOTE: Amount of antibody per unit planar surface area (single side) of mesh

EXAMPLE 8

An aromatic analogue of the secondary intermediate with a sulfur spacer arm described in Example 2 was prepared by soaking the membrane of Example 1 in an ethanolic solution of p-phenylene diamine (5.4%) for 15 minutes at room temperature. It was then washed with water. The presence of amine groups was confirmed by staining with an aqueous solution of 4-nitrobenzenediazonium tetrafluoroborate.

Although the structure of the intermediate has not been proven, the presence of sulphonyl groups has been positively established (see Example 1). Therefore, the intermediate contains one or both of the following structures:

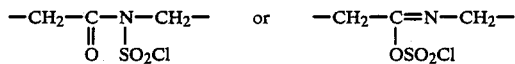

which represents tautomeric structures.

Various other modifications of the processes and products of the invention may be made without departing from the scope and ambit of the invention.

We claim:

1. A process for producing a support capable of reaction with antibodies or enzymes, said process comprising the steps of:
    (i) reacting an aliphatic polyamide with a solution consisting essentially of sulphuryl chloride and a paraffin or cycloparaffin to produce a sulphuryl chloride modified polyamide reactive intermediate product;
    (ii) reacting the product of step (i) with a compound that binds to said product to provide a covalent chemical link to which antibodies or enzymes may be bound.

2. A process according to claim 1 wherein the product of step (i) is reacted with 2,3-epoxy-1-chloropropane to provide epoxide groups as the covalent chemical link.

3. A support capable of reaction with antibodies or enzymes prepared by a process comprising the steps of:
    (i) reacting an aliphatic polyamide with a solution consisting essentially of sulphuryl chloride and a paraffin or cycloparaffin to produce a sulphuryl chloride modified polyamide reactive intermediate product;
    (ii) reacting the product of (i) with a compound that binds to said product to provide a covalent chemical link to which antibodies or enzymes may be bound.

4. A support according to claim 3 wherein the product of step (i) is reacted with 2,3-epoxy-1-chloropropane to provide epoxide groups as the covalent chemical link.

* * * * *